United States Patent
Kraemer et al.

(10) Patent No.: US 10,470,729 B2
(45) Date of Patent: Nov. 12, 2019

(54) CARRYING DEVICE

(71) Applicant: Siemens Healthcare GmbH, Erlangen (DE)

(72) Inventors: Alexander Kraemer, Irchenrieth (DE); Michael Meyer, Hausen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 15/962,141

(22) Filed: Apr. 25, 2018

(65) Prior Publication Data

US 2018/0310904 A1 Nov. 1, 2018

(30) Foreign Application Priority Data

Apr. 28, 2017 (EP) .................................. 17168761

(51) Int. Cl.
*A61B 6/00* (2006.01)

(52) U.S. Cl.
CPC .......... *A61B 6/4441* (2013.01); *A61B 6/4464* (2013.01)

(58) Field of Classification Search
CPC .... A61B 6/4441; A61B 6/4458; A61B 6/4464
USPC .......................................... 378/62, 193–198
See application file for complete search history.

(56) References Cited

U.S. PATENT DOCUMENTS

| 2011/0280379 A1* | 11/2011 | Maschke ............... A61B 6/4411 378/196 |
| 2014/0086393 A1 | 3/2014 | Graumann |
| 2014/0177799 A1 | 6/2014 | Noda |
| 2015/0216494 A1 | 8/2015 | Atzinger |

FOREIGN PATENT DOCUMENTS

| CN | 204909477 U | * 12/2015 | .......... A61B 6/4441 |
| CN | 204909477 U | 12/2015 | |
| DE | 102010020603 A1 | 11/2011 | |

(Continued)

OTHER PUBLICATIONS

Extended European Search Report and English translation thereof dated Jul 6, 2017.

(Continued)

*Primary Examiner* — Courtney D Thomas
(74) *Attorney, Agent, or Firm* — Harness, Dickey & Pierce, P.L.C.

(57) ABSTRACT

A carrying device is disclosed for a retaining device for an X-ray tube assembly and an X-ray detector of an X-ray system. The carrying device includes a suspension device; a first carrier element arranged on the suspension device; a second carrier element; a first connecting element, the second carrier element being connected to the first carrier element via the first connecting element; a third carrier element connectable to the retaining device; and a second connecting element, the third carrier element being connected to the second carrier element via the second connecting element. In an embodiment, the first connecting element and/or the second connecting element include a revolute joint. Further, the distance between the suspension device and the first connecting element is variable via the first carrier element, and the distance between the first connecting element and the second connecting element is variable via the second carrier element.

17 Claims, 6 Drawing Sheets

(56) References Cited

FOREIGN PATENT DOCUMENTS

| | | |
|---|---|---|
| DE | 102012208850 A1 | 4/2013 |
| DE | 102012217072 A1 | 3/2014 |
| DE | 102014202013 A1 | 8/2015 |
| DE | 102015202082 A1 | 12/2015 |

OTHER PUBLICATIONS

European Intention to Grant and English translation thereof dated May 12, 2018.
Extended European Search Report #17168761.9 dated Jul. 6, 2017.
Chinese Office Action and English translation thereof dated Jun. 25, 2019.

* cited by examiner

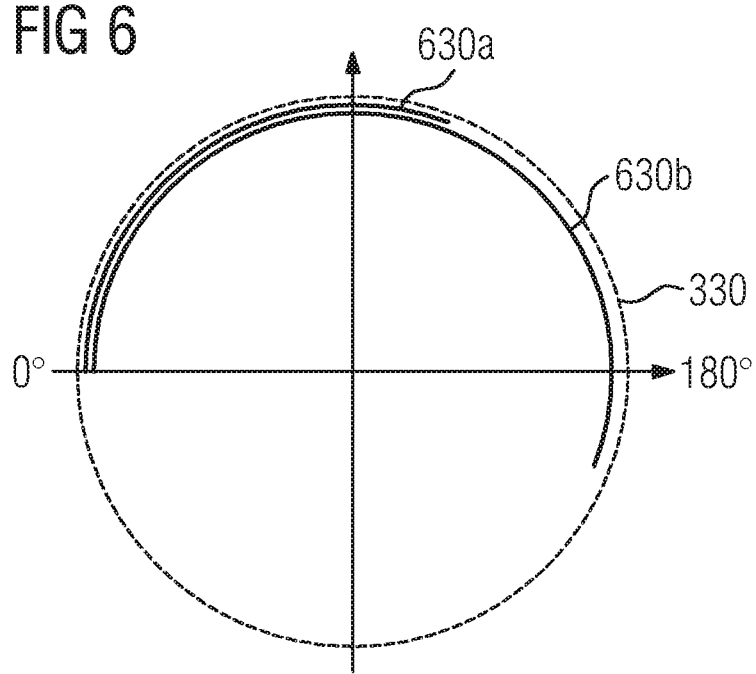

CARRYING DEVICE

PRIORITY STATEMENT

The present application hereby claims priority under 35 U.S.C. § 119 to European patent application number EP 17168761.9 filed Apr. 28, 2017, the entire contents of which are hereby incorporated herein by reference.

FIELD

At least one embodiment of the invention generally relates to a carrying device for a retaining device for an X-ray tube assembly and an X-ray detector of an X-ray system, as well as to an X-ray system.

BACKGROUND

In the medical technology field, use is often made of carrying devices which can be connected to retaining devices and are either suspended from a ceiling or anchored to the floor. An X-ray system typically comprises at least one carrying device and a retaining device for an X-ray unit. The X-ray unit typically comprises an X-ray tube assembly and an X-ray detector.

In certain applications, in interventional angiography or coronary angiography for example, the carrying device is sometimes variably adjustable via a motor-driven remote control. A carrying device embodied in such a way can vary or releasably lock the position of the retaining device arranged thereon continuously or discretely in at least one spatial direction or around at least one spatial axis. This serves in particular for positioning and aligning the retaining device. Usually, the X-ray unit can also be flexibly adjusted around the patient arranged on a cantilevered tabletop, in particular a patient couch. Preferably, an optimal treatment of a patient can therefore be performed via the X-ray unit.

Carrying devices are known which are either suspended from the ceiling or anchored to the floor and are connected to a retaining device, the retaining device having a C-arm with an X-ray unit arranged at the ends thereof. The retaining device often has further elements that serve for the orientation of the X-ray unit. The suspension device can be installed on the floor or ceiling of an examination room either in a fixed location or movably, in particular mounted on rails.

A ceiling-mounted medical X-ray machine is disclosed in DE 10 2015 202 082 A1, an X-ray tube assembly and an X-ray detector being movable about an orbital axis via a traveling C-arm and a G-arm arranged thereon.

An X-ray device is known from DE 10 2014 202 013 A1 which comprises a C-arm having, rotatably mounted thereon, a radiation detector which is rotatable by way of a motorized drive means.

DE 10 2012 208 850 A1 describes an X-ray device for the acquisition of radiation images, comprising a radiation source and a radiation receiver which are arranged on a common C-arm that is arranged on a ceiling-mounted load-bearing structure, the C-arm being arranged on the load-bearing structure so as to be rotatable around an isocenter, as well as a substantially rectangular patient couch and a control device, the load-bearing structure being movable on the ceiling side both in parallel with and perpendicular to the longitudinal direction of the patient table at least at right angles to the longitudinal axis also during the image acquisition taking place while the C-arm is rotating.

SUMMARY

At least one embodiment of the invention discloses a carrying device for a retaining device for an X-ray tube assembly and an X-ray detector of an X-ray system, which carrying device enables a flexible movement of the connectable retaining device.

Advantageous developments are set forth in the claims.

At least one embodiment of the invention discloses a carrying device, for a retaining device for an X-ray tube assembly and an X-ray detector of an X-ray system, comprising:
a suspension device,
a first carrier element arranged on the suspension device,
a second carrier element,
a first connecting element, wherein the second carrier element is connected to the first carrier element via the first connecting element,
a third carrier element which can be connected to the retaining device, and
a second connecting element, wherein the third carrier element is connected to the second carrier element via the second connecting element,
wherein the first connecting element and/or the second connecting element have/has a revolute joint, the distance between the suspension device and the first connecting element is variable via the first carrier element, and
the distance between the first connecting element and the second connecting element is variable via the second carrier element.

An X-ray system comprising:
an X-ray tube assembly;
an X-ray detector;
a carrying device including
  a suspension device,
  a first carrier element arranged on the suspension device,
  a second carrier element,
  a first connecting element, the second carrier element being connected to the first carrier element via the first connecting element,
  a third carrier element, and
  a second connecting element, the third carrier element being connected to the second carrier element via the second connecting element,
  wherein at least one of the first connecting element and the second connecting element include a revolute joint, a distance between the suspension device and the first connecting element being variable via the first carrier element and a distance between the first connecting element and the second connecting element being variable via the second carrier element;
a retaining device, connected to the third carrier element and including a C-arm, the X-ray tube assembly and the X-ray detector being arranged at ends of the C-arm; and
a connecting device, the X-ray tube assembly and the X-ray detector being arranged so as to be movable exclusively via a movement of the C-arm relative to the connecting device along a first path, defined by a shape of the C-arm, part of a circle of rotation and an arc length of the C-arm corresponding to a first angle An X-ray system according to at least one embodiment of the invention comprising:
an inventive carrying device of at least one embodiment, and
a retaining device connected to the third carrier element, the retaining device having a C-arm at the ends of which an X-ray tube assembly and an X-ray detector are arranged, and a connecting device, wherein the X-ray tube assembly and the X-ray detector are arranged so as to be movable exclusively via a movement of the C-arm relative to the connecting device along a first path which is predefined by the shape of the C-arm and is part of a circle of rotation and the arc length of which corresponds to a first angle.

BRIEF DESCRIPTION OF THE DRAWINGS

Further advantages and details of the present invention will emerge from the example embodiments described in the following, as well as with reference to the drawing, in which:

FIG. 6 shows a circle of rotation.

DETAILED DESCRIPTION OF THE EXAMPLE EMBODIMENTS

Figure 1:
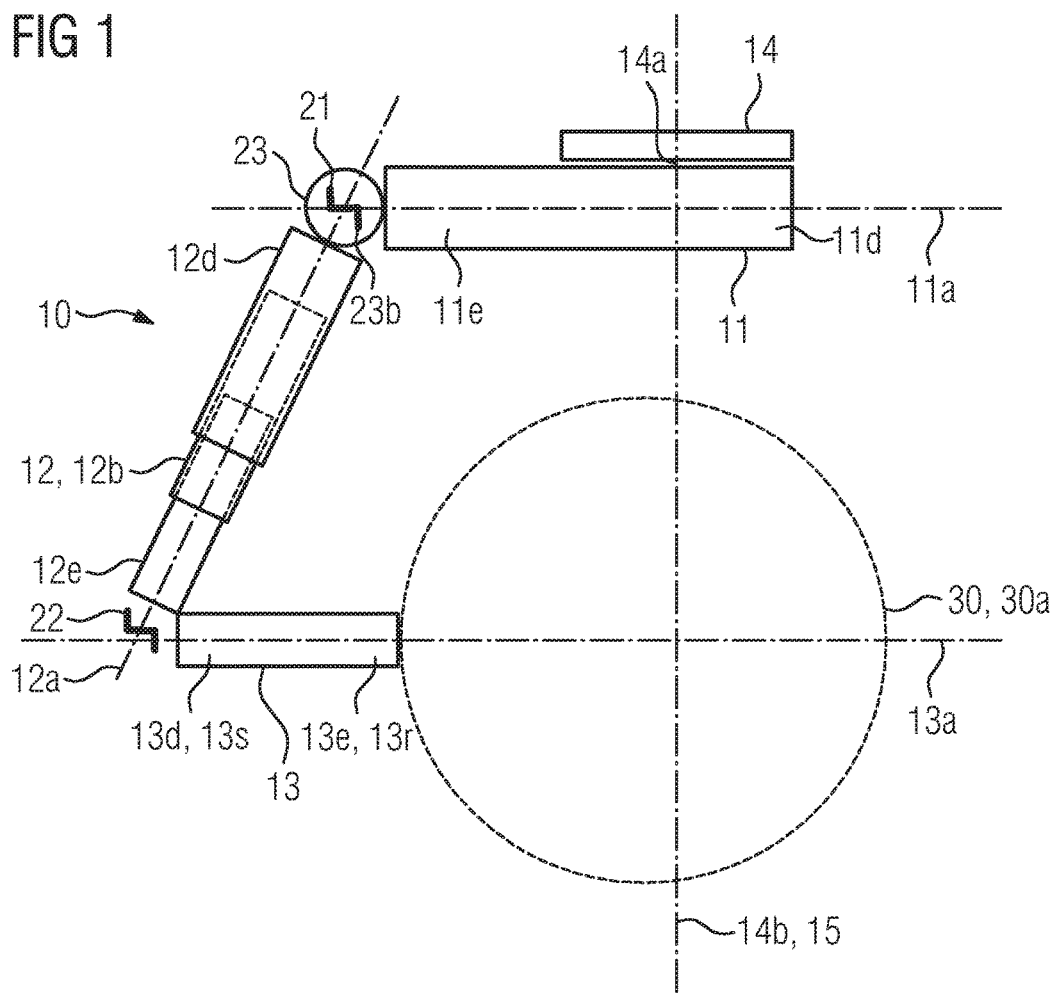
FIG. 1 shows a first embodiment variant of a carrying device.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention discloses a carrying device, for a retaining device for an X-ray tube assembly and an X-ray detector of an X-ray system, comprising:

a suspension device, a first carrier element arranged on the suspension device, a second carrier element, a first connecting element, wherein the second carrier element is connected to the first carrier element via the first connecting element, a third carrier element which can be connected to the retaining device, and a second connecting element, wherein the third carrier element is connected to the second carrier element via the second connecting element, wherein the first connecting element and/or the second connecting element have/has a revolute joint, the distance between the suspension device and the first connecting element is variable via the first carrier element, and the distance between the first connecting element and the second connecting element is variable via the second carrier element.

In this way, embodiments of the inventive carrying device are able to permit a multidimensional kinematic movement and therefore to allow the displacement of the carrying device in space, in particular a flexible positioning of the third carrier element. At least one embodiment of the invention therefore offers in particular several advantages:

1) Given a suitable embodiment of the carrying device, the third carrier element can be in particular height-adjustable via the carrying device. If a retaining device is connected to the carrying device, the retaining device, in particular the X-ray unit, can be height-adjustable preferably via the carrying device. For example, a vertical isocenter shift can be performed via the carrying device, the isocenter of the X-ray unit in particular being displaceable and/or releasably lockable on a straight line along an axis standing in particular perpendicularly on the floor or ceiling.

2) The carrying device can have an additional degree of freedom along the first carrier element. Usually, a carrying device can execute a movement in particular of the connected retaining device along the first carrier element only if the suspension device is mounted on rails. Due to mechanical design constraints, the movement of the suspension device along rails often is possible only in two spatial directions, which preferably stand at right angles to one another, one spatial direction being parallel to a patient couch, for example, and another spatial direction standing perpendicular thereto. Via a suitable arrangement of the first carrier element on the suspension device and a corresponding embodiment of the inventive carrying device, the retaining device, in particular the X-ray unit, is displaced for example in a direction that may be parallel to a ceiling or to a floor. Preferably, the displacement of the retaining device can take place in the horizontal direction. Typically, the displacement of the retaining device can take place in a direction parallel to the ceiling or floor without any movement of the suspension device relative to the ceiling or floor. This enables off-center regions of the patient to be irradiated more easily, for example.

3) The carrying device can preferably be embodied in such a way that the third carrier element is displaceable in particular along a circular path. Preferably, one end of the third carrier element at which the third carrier element can be connected to the retaining device is displaceable along the circular path. Typically, this is possible by a combination of the adjustment of the revolute joint, the varying of the distance between the suspension device and the first connecting element via the first carrier element and the varying of the distance between the first connecting element and the second connecting element via the second carrier element.

The suspension device is preferably embodied for arranging, in particular for fixing, the carrying device on a ceiling or a floor, in particular in an examination room. Typically, the suspension device is releasably fixed on the ceiling or the floor. The carrying device is usually embodied in such a way that, for example, the first carrier element is connected to the ceiling of the examination room via the suspension device. The suspension device may for example have a ceiling-mounted carriage and be embodied in such a way that it is mounted on rails of a first rail plane. This can in particular enable a displacement of the suspension device along the rails of the first rail plane and locking of the suspension device on the rails of the first rail plane.

Furthermore, it is also conceivable that the suspension device is mounted on a second rail plane in such a way that a displacement of the suspension device along the rails of the second rail plane and locking of the suspension device on the rails of the second rail plane can be performed alternatively or in addition to the displacement on the first rail plane. For example, the suspension device, in particular the ceiling-mounted carriage, can be mounted on the rails of the first rail plane, which are in turn arranged on the rails of the second rail plane. The ceiling-mounted carriage can have suitable device(s) in order to move the suspension device on the first rail plane or the second rail plane. The first rail plane or the second rail plane may also be part of the suspension device. Above all, the first rail plane and/or the second rail plane may be embodied in such a way that the first rail plane can in particular be movable relative to the second rail plane. Preferably, the rails of the rail planes are embodied as straight. Generally, the rail planes are aligned parallel to the floor or to the ceiling. In particular, the longitudinal axes extending in the longitudinal direction of the rail planes may stand at right angles to one another. It follows from this that in this case the suspension device can be movable in two spatial directions.

The first carrier element is arranged on the suspension device. This arrangement can be embodied in accordance with a fixing. Typically, the first carrier element is arranged on the suspension device in such a way that the first carrier element can be displaceable relative to the suspension device. Alternatively or in addition, the fixing may be rigid.

One embodiment variant provides that the suspension device comprises a device for arranging the first carrier element in such a way that the first carrier element is mounted so as to be rotatable about a system axis of the carrying device which, when the carrying device is suspended from the ceiling or anchored to the floor, stands perpendicularly on the ceiling or floor. Usually, the system axis extends through the suspension device, in particular through a center of rotation of the suspension device about which the first carrier element is rotatably mounted. The first carrier element can therefore be mounted so as to be rotatable about the system axis, at least one end of the first carrier element being able to be moved onto a circle of rotation, the plane of which circle of rotation is plane-parallel to the ceiling. The advantageous height adjustability of the third carrier element which can be made possible by the carrying device is usually effected parallel to or in particular along the system axis.

According to one embodiment variant, the first carrier element is embodied as displaceable relative to the suspension device. Typically, the distance between the suspension device and the first connecting element can be variable via the first carrier element, which is embodied as displaceable relative to the suspension device. Usually, the first carrier element can be arranged on the suspension device in such a way that the first carrier element is mounted so as to be displaceable relative to the suspension device, in particular at a suspension point of the suspension device. Normally, the suspension point can correspond to the center of rotation about the system axis. Usually, the first carrier element has a first end and a second end, the first end and the second end being arranged on opposite sides along a longitudinal axis extending in the longitudinal direction of the first carrier element.

The second end of the first carrier element is usually connected to the second carrier element via the first connecting element. Via the first carrier element that is displaceable relative to the suspension device, the second end of the first carrier element can for example be shifted closer to the suspension point, while at the same time the first end of the first carrier element can be moved further away from the suspension point, and vice versa.

If the first carrier element is embodied as displaceable relative to the suspension device, the suspension device may also have a device to enable a displacement of the type. Usually, the first carrier element can be embodied as displaceable along the longitudinal axis of the first carrier element.

Typically, the displacement of the first carrier element which is embodied as displaceable relative to the suspension device can mean that the first end of the first carrier element and the second end of the first carrier element can be displaced along the longitudinal axis to the same extent and in the same direction. In this case, the distance between the first end of the first carrier element and the second end of the first carrier element, or the length of the first carrier element, can usually remain constant. The first carrier element may also be arranged on the suspension device in such a way that the longitudinal axis of the first carrier element stands perpendicularly on the system axis, as a result of which the advantageous horizontal displacement of the retaining device can be made possible.

According to a further embodiment variant, the first carrier element is embodied as telescopic. Typically, the distance between the suspension device and the first connecting element may also be variable via a first carrier element that is embodied as telescopic. In this case, the second end of the first carrier element can for example be shifted closer to the suspension point, while the first end of the first carrier element maintains a constant distance from the suspension point.

It is conceivable, if the first carrier element is only telescopic, that the first end of the first carrier element is arranged on the suspension device. For example, the first carrier element can have a telescope unit which can be retracted and extended. In contrast to the embodiment variant wherein the first carrier element is embodied as displaceable, the distance between the two ends of the first carrier element can be varied when the telescope unit is retracted or extended. There is usually a change in the length of the first carrier element in this case. The two ends of the first carrier element are usually moved further away from each other when the telescope unit of the first carrier element is extended than when the telescope unit of the first carrier element is retracted. The retraction or extension of the telescope unit corresponds to a telescopic displacement. When retracted, the telescope unit can usually become smaller, and when extended, the telescope unit can usually become bigger.

According to a further embodiment, it is conceivable that the first carrier element is embodied as telescopic and displaceable relative to the suspension device.

The second carrier element is connected to the first carrier element via the first connecting element, in particular in such a way that an angle not equal to 0 is present between the first carrier element and the second carrier element. In other words, the longitudinal axis of the first carrier element and a longitudinal axis extending in the longitudinal direction of the second carrier element are in particular not parallel. Typically, a first plane of rotation may be defined by the longitudinal axis of the first carrier element and by the longitudinal axis of the second carrier element.

According to a further embodiment variant, the second carrier element is embodied as displaceable relative to the first connecting element. In particular, the first connecting element may have a device to enable the second carrier element to be displaceable relative to the first connecting element along a longitudinal axis extending in the longitudinal direction of the second carrier element. The second carrier element may for example be mounted on rails of the first connecting element, on which the second carrier element can be guided via the first connecting element. The second carrier element usually has a first end and a second end. The first end of the second carrier element and the second end of the second carrier element are in this case arranged in particular along the longitudinal axis of the second carrier element on opposite sides of the second carrier element.

Typically, if the first end of the second carrier element is shifted away from the first connecting element along the longitudinal axis of the second carrier element, the second end of the second carrier element can simultaneously be shifted closer to the first connecting element, and vice versa. Preferably, the distance between the two ends of the second carrier element, in particular the length of the second carrier element, can remain constant.

According to a further embodiment, the distance between the first connecting element and the second connecting element is variable via the second carrier element if the second carrier element is embodied as telescopic. In this case, the second carrier element has for example a telescope unit which can be retracted and extended. The distance between the first connecting element and the second connecting element may become either smaller or greater due to the retraction or extension of the telescope unit. According to a further embodiment, if the second carrier element is embodied only as telescopic, the first end of the second carrier element can be connected to the first connecting element and the second end of the second carrier element can be connected to the second connecting element.

According to a further embodiment variant, the second carrier element is embodied as telescopic and displaceable relative to the first connecting element.

In one embodiment, at least the first carrier element or the second carrier element is preferably embodied only as telescopic, as a result of which a risk of collision of, for example, a user with the telescopically embodied carrier element can be reduced. The risk of collision is usually based on the length of a carrier element remaining constant when it is embodied only as displaceable. The user is usually a person that is present in the examination room, for example a patient or a physician. It is sometimes conceivable that a number of users may also be present in the examination room.

In a further embodiment variant, both the first carrier element and the second carrier element are embodied only as telescopic. This is advantageous insofar as this makes the risk of collision of the carrier elements in particular with the user even smaller than when at least one carrier element is embodied only as displaceable. If both the first carrier element and the second carrier element are embodied only as telescopic, the length of the respective carrier element is varied via the retraction or extension of the respective telescope unit. A carrier element that is embodied as displaceable, on the other hand, requires free space for collision-free operation. If the distance between the suspension device and the first connecting element is reduced for example via a first carrier element that is embodied as only displaceable relative to the suspension device, the first end of the first carrier element can be pushed into the free space. Furthermore, carrier elements that are only telescopic can permit more compact designs.

The second connecting element connects the second carrier element and the third carrier element preferably in such a way that an angle not equal to 0 is present between the second carrier element and the third carrier element. In other words, the longitudinal axis of the second carrier element and a longitudinal axis extending in the longitudinal direction of the third carrier element are in particular not parallel. Typically, a second plane of rotation may be defined by the longitudinal axis of the second carrier element and by the longitudinal axis of the third carrier element.

According to a further embodiment variant, the third carrier element is embodied as rotatable relative to the second connecting element about a longitudinal axis extending in the longitudinal direction of the third carrier element. Usually, a first end of the third carrier element can be connected to the second connecting element. The third carrier element is preferably embodied in such a way that the retaining device can be connected at a second end of the third carrier element. The first end of the third carrier element and the second end of the third carrier element generally lie on opposite sides of the third carrier element along the longitudinal axis of the third carrier element. Typically, in particular the second end of the third carrier element is mounted as rotatable relative to the second connecting element about the longitudinal axis of the third carrier element.

The longitudinal axis of the third carrier element may be called the angular axis. The angular axis typically corresponds to the axis of rotation of the third carrier element. The second end of the third carrier element can therefore be rotatable with respect to the first end of the third carrier element, while the first end of the third carrier element remains rigid.

It is therefore conceivable that the third carrier element has a stator and a rotor. The first end of the third carrier element can usually have the stator, and the second end of the third carrier element the rotor. The third carrier element may for example be embodied in such a way that the rotor of the third carrier element is mounted so as to be rotatable relative to the second connecting element, in particular relative to the stator of the third carrier element, about the longitudinal axis of the third carrier element. Usually, the stator may be rigidly connected to the second connecting element.

Basically, it is also conceivable in a further embodiment that the third carrier element is embodied as displaceable and/or telescopic relative to the second connecting element.

If the retaining device is connected to the second end of the third carrier element, a movement of the retaining device described about the angular axis may also be referred to as a propeller movement, because then the retaining device may be mounted as rotatable relative to the second connecting element in a similar manner to a propeller of an aircraft. This is advantageous in particular during the examination of a patient, because in that way, for example, the collision of the retaining device both with the user and with the patient can be avoided. In particular, such an angular movement of the retaining device enables the X-ray unit to be positioned around the patient in a flexible manner, while at the same time the imaging can be performed more easily and in particular also a higher image quality can be achieved.

The revolute joint usually has suitable device(s) to rotate the respective carrier elements connected to the revolute joint relative to one another. The revolute joint can in particular vary or releasably lock the angle between the carrier elements connected to the revolute joint.

If the first connecting element has the revolute joint, the second carrier element can be rotated in particular about a first axis of rotation with respect to the first carrier element. The first axis of rotation preferably extends through the first connecting element and stands perpendicularly on the first plane of rotation. Preferably, the angle between the first carrier element and the second carrier element can be variable. According to a further embodiment, only the first connecting element has the revolute joint.

If the second connecting element has the revolute joint, the third carrier element can be rotated in particular about a second axis of rotation with respect to the second carrier element. The second axis of rotation preferably extends through the second connecting element and stands perpendicularly on the second plane of rotation. Preferably, the angle between the second carrier element and the third carrier element can be variable. According to a further embodiment, only the second connecting element has the revolute joint.

If only the first connecting element or only the second connecting element has the revolute joint or if both the first connecting element and the second connecting element each have a revolute joint, the third carrier element, in particular the second end of the third carrier element, can be movable on the circular path. Furthermore, the third carrier element can also be height-adjustable in this case.

The X-ray system according to an embodiment of the invention comprises:
an inventive carrying device of at least one embodiment, and
a retaining device connected to the third carrier element, the retaining device having a C-arm at the ends of which an X-ray tube assembly and an X-ray detector are arranged, and a connecting device,
wherein the X-ray tube assembly and the X-ray detector are arranged so as to be movable exclusively via a movement of the C-arm relative to the connecting device along a first path which is predefined by the shape of the C-arm and is part of a circle of rotation and the arc length of which corresponds to a first angle.

The X-ray system may preferably be embodied as an angiography system, the angiography system preferably being suitable for performing an angiographic measurement.

The retaining device can be connected in particular to the third carrier element via the connecting device. According to an embodiment, the connecting device can preferably be rotated about the angular axis which corresponds to the longitudinal axis of the third carrier element. If the connecting device can be rotated about the angular axis, then normally the retaining device and in particular the C-arm can be rotated simultaneously about the angular axis. For example, the connecting device can have a suspension point at which the connecting device, in particular the retaining device, is connected to the third carrier element. Preferably, the suspension point of the connecting device can be arranged at the second end of the third carrier element. The arrangement of the suspension point of the connecting device at the second end of the third carrier element can correspond to a fixing.

The C-arm can usually enable an examination region in a patient to be positioned on an imaginary line between the two ends of the C-arm. The C-arm can usually have the X-ray unit, the X-ray tube assembly being arranged at a first end of the C-arm, and the X-ray detector at a second end of the C-arm. Typically, the C-arm has a shape in particular in the form of a segment of a circle. Alternatively, it is also conceivable for the C-arm to have a different shape, for example a partially angular shape, possibly a shape in the form of an open half-rectangle. The embodiment of the C-arm in the form of a segment of a circle can be advantageous in particular in comparison with a different C-arm that is embodied in the form of an open half-rectangle, because the embodiment of the C-arm in the form of a segment of a circle can reduce the risk of collision with a patient.

An orbital axis can stand in particular perpendicularly on a C-arm plane defined by the shape of the C-arm. Furthermore, the first path on which the X-ray unit can be arranged so as to be movable relative to the connecting device can usually be predefined by the shape of the C-arm. The movement of the X-ray unit in the C-arm plane can correspond to an orbital movement. The X-ray unit, in particular the X-ray tube assembly and the X-ray detector, can therefore be moved in the C-arm plane about an orbital axis of rotation along an orbital circle of rotation. The orbital axis of rotation usually corresponds to the orbital axis. Preferably, the X-ray unit, in particular the X-ray tube assembly and the X-ray detector, can be moved along the first path having an arc length, wherein a first circle of rotation can have the first path. Each arc length is contained in a circle having a respective radius. The arc length of the first path, for example, can usually be converted into a first angle via a radius of the respective circle that has the first path. The arc length of the first path therefore corresponds to the first angle.

Preferably, the retaining device can be moved on the first path exclusively via a movement of the C-arm relative to the connecting device. For this purpose, the connecting device can have suitable means, for example a carriage, which is connected to the C-arm in such a way that the C-arm is movable relative to the connecting device. For example, the C-arm can have rollers that are guided on rails of the carriage. If the X-ray unit can be displaced with respect to the carriage, this can correspond in particular to a displacement of the X-ray unit relative to the connecting device. The connecting device can also have further a device that can allow a displacement of the X-ray unit relative to the connecting device. Usually, the X-ray unit is also embodied accordingly. Alternatively or in addition to the carriage, the connecting device can have a third rail plane, the C-arm being mounted so as to be movable on the rails of the third rail plane. The third rail plane can make it possible for the C-arm, in particular the X-ray tube assembly and the X-ray detector, to travel along the first path.

According to a suitable embodiment, the carrying device can perform a movement of the third carrier element along the circular path, a first circle of rotation preferably having the circular path. The retaining device can be displaced relative to the connecting device on a second circle of rotation. An embodiment in which the first circle of rotation corresponds to the second circle of rotation and also to the orbital circle of rotation is particularly preferred. The first circle of rotation, the second circle of rotation and the orbital circle of rotation are preferably congruent to the circle of rotation. The second path can be part of the circle of rotation to the extent that the second path is contained in the orbital circle of rotation. In particular, the arc length of the second path can be congruent with a section of the circular path of the circle of rotation.

The X-ray unit can usually be movable on the orbital circle of rotation between a first extreme position and a second extreme position. The movement between the first extreme position and the second extreme position along the circle of rotation, in particular the orbital circle of rotation, is accomplished via a configuration of the carrying device in combination with the X-ray unit that is movable relative to the connecting device. According to a further embodiment variant, the X-ray tube assembly and the X-ray detector are arranged via the first carrier element, the revolute joint, the second carrier element and the movement of the C-arm relative to the connecting device so as to be movable along a second path which is part of the circle of rotation and the arc length of which corresponds to a second angle, the second angle being greater than the first angle. For example, the first extreme position and the second extreme position of the X-ray tube assembly and the X-ray detector are defined by the second angle.

According to an embodiment variant, the second angle equals at least 200°, which usually is advantageous for three-dimensional (3D) imaging. In this way it is possible for the orbital movement to be effected over an arc length that corresponds at least to an angle of 200°. The orbital movement through at least 200° is typically necessary to ensure the correct functioning of the image reconstruction process during the three-dimensional imaging when an angiographic measurement of the patient is performed. No C-arms having an arc length corresponding to an angle greater than 180° are employed due to the risk of collision between the retaining device and the patient or, as the case may be, the large-scale embodiment inherent in the design. For this reason, the C-arm can usually be mounted so as to be movable relative to the connecting device.

Due to structures such as the X-ray tube assembly and detector, a multilevel retaining device is typically necessary for performing the orbital movement in conventional X-ray systems. A multilevel retaining device of the type in conventional X-ray systems has for example a carriage which comprises a further telescopic carriage which is movable on a circular path and in which the C-arm movably mounted on a roller bearing can be guided. It follows from this that the multilevel retaining device of the type in conventional X-ray systems usually has an orbital telescope unit which, in contrast to the telescope unit of the carrier elements, is movable, not along a straight line, but on a circular path. In this connection, a retaining device of the type also has a G-arm in addition to the C-arm, the orbital telescope unit usually having the C-arm and the G-arm. The G-arm can be arranged so as to be movable relative to the C-arm and the C-arm can be arranged so as to be movable relative to the carriage. The multilevel retaining device of the type often has recourse to an embodiment having the G-arm and the C-arm as part of the orbital telescope unit. A multilevel retaining device of the type can therefore perform the orbital movement of the X-ray unit through 200°.

According to an inventive embodiment, the retaining device will in particular have no orbital telescope unit, but instead the carrying device can perform the orbital movement of the X-ray unit through at least 200° together with the retaining device. Owing to its design, the X-ray system is therefore advantageously smaller compared to a different X-ray system having a multilevel retaining device, as a result of which the X-ray system can for example also be used in smaller examination rooms.

According to a further embodiment, the retaining device is height-adjustable along the system axis via the first carrier element, the revolute joint and the second carrier element. The carrying device can be embodied in such a way that the retaining device is height-adjustable only along the system axis or parallel to the system axis. Also, only certain components of the retaining device may preferably be height-adjustable, for example the X-ray unit. In order to move the X-ray unit from a lower to a higher position, the distance between the first connecting element and the suspension device can for example be increased, while the distance between the first connecting element and the second connecting element can be reduced. For example, the X-ray system can also be height-adjustable only via a changing of the distance between the first connecting element and the second connecting element if preferably the longitudinal axis of the second carrier element is parallel to the system axis. The respective distance can be differently variable depending on the embodiment of the carrier elements: for example via a telescopic displacement of the telescope unit or via a displacement of the respective carrier element referred to the respective suspension point, i.e. for example via a displacement of the first carrier element relative to the suspension device or in particular via a displacement of the second carrier element relative to the first connecting element.

A height adjustability of the retaining device is in particular advantageous when the patient couch is height-adjustable and the user is able for example to adjust the height of the patient couch and the retaining device to match each other. This is in particular to the benefit of the health of the user or is also advantageous for example when performing an interventional procedure which can be carried out on the patient couch before, after or during an angiographic measurement.

According to an embodiment variant, the distance between the X-ray tube assembly and the X-ray detector is variable. The distance between the X-ray tube assembly and the X-ray detector can be variable in such a way that the distance between the X-ray tube assembly and the X-ray detector can be varied only via a suitable configuration of the retaining device. Usually, the X-ray detector can have a telescope unit which can be retracted and extended. This usually serves for focusing the X-ray radiation and/or in particular for aligning the isocenter. In particular, the X-ray detector can be mounted such that the X-ray detector is rotatable about an axis which corresponds to a line between the X-ray tube assembly and the X-ray detector and usually stands perpendicularly on the X-ray detector surface.

FIG. 1 shows a first embodiment variant of a carrying device 10. The carrying device 10 for a retaining device for an X-ray tube assembly and an X-ray detector of an X-ray system comprises a suspension device 14, a first carrier element 11 arranged on the suspension device 14, a second carrier element 12 and a first connecting element 21. The second carrier element 12 is connected to the first carrier element 11 via the first connecting element 21. In addition, the carrying device 10 comprises a third carrier element 13, which can be connected to the retaining device, and a second connecting element 22, the third carrier element 13 being connected to the second carrier element 12 via the second connecting element 22. In the case shown in FIG. 1, the first connecting element 21 has a revolute joint 23.

The distance between the suspension device 14 and the first connecting element 21 is variable via the first carrier element 11, and the distance between the first connecting element 21 and the second connecting element 22 is variable via the second carrier element 12.

The first carrier element 11 is displaceable relative to the suspension device 14 and the second carrier element 12 is embodied as telescopic. Further embodiments are conceivable, for example that the first carrier element 11 is embodied as telescopic and the second carrier element 12 is embodied as displaceable relative to the first connecting element 21. It is also conceivable that the first carrier element 11 and the second carrier element 12 are embodied as telescopic.

In this example, the suspension device 14 is embodied for an arrangement of the first carrier element 11 on a ceiling of the examination room. The carrying device 10 has a system axis 15 which, when the carrying device 10 is suspended from the ceiling or anchored to the floor, stands perpendicularly on the ceiling or the floor and extends through the suspension device 14. The first carrier element 11 is mounted on the suspension device 14 so as to be rotatable about the system axis 15. The first carrier element may also be mounted so as to be rotatable about an axis of rotation 14b of the suspension device 14. In this embodiment, the axis of rotation 14b of the suspension device 14 corresponds to the system axis 15. The system axis 15 extends through a suspension point 14a and is aligned vertically. The first carrier element 11 is arranged at the suspension point 14a by way of a suspension means, for example is mounted on rollers or rails or in particular is fixed. The suspension device 14 is dimensioned smaller along the system axis 15 than perpendicularly to the system axis 15. The suspension device 14 is embodied in particular as flat.

The first carrier element 11 has a longitudinal axis 11a which extends in the longitudinal direction of the first carrier element 11 and represents the axis of displacement of the first carrier element 11 relative to the suspension device 14. In addition, the first carrier element has a first end 11d of the first carrier element 11 and a second end 11e of the first carrier element 11. The longitudinal axis 11a of the first carrier element 11 stands perpendicularly on the system axis 15 and is accordingly aligned horizontally. The first carrier element 11 is able to vary the distance between the suspension device 14, in particular the suspension point 14a, and the first connecting element 21. For example, if the distance between the suspension device 14 and the first connecting element 21 becomes smaller, the distance between the suspension device 14 and the first end 11d of the first carrier element 11 simultaneously becomes greater. The first carrier element 11 is therefore displaced along the longitudinal axis 11a of the first carrier element 11 relative to the suspension device 14 without the distance between the first end 11d of the first carrier element 11 and the second end 11e of the first carrier element 11 being varied. If the first carrier element 11 is displaced along the longitudinal axis 11a of the first carrier element 11, the first connecting element 21, the second carrier element 12, the second connecting element 22 and the third carrier element 13, inter alia, are simultaneously displaced to the same extent along the longitudinal axis 11a. If the first carrier element 11 is displaced relative to the suspension device 14, the retaining device which can be connected to the third carrier element 13 is also displaced. In this case the extension of the first carrier element 11 in the longitudinal direction 11a, that is to say the length of the first carrier element 11, remains constant.

The second carrier element 12 has a longitudinal axis 12a which extends in the longitudinal direction of the second carrier element 12 and along which the distance between the first connecting element 21 and the second connecting element 22 can be varied. In addition, the second carrier element 12 has a first end 12d of the second carrier element 12 and a second end 12e of the second carrier element 12. The second carrier element 12 has a telescope unit 12b which can be retracted and extended. When the telescope unit 12b is retracted, the distance between the first end 12d of the second carrier element 12 and the second end 12e of the second carrier element 12 is reduced, the distance between the first connecting element 21 and the second connecting element 22 also being reduced accordingly. The connecting element 22 and consequently also the carrier element 13 are therefore displaced along the longitudinal axis 12a relative to the connecting element 21 via the second carrier element 12, in particular via the telescope unit 12b of the second carrier element 12. In the telescopic displacement via the telescope unit 12b, the extension of the second carrier element 12 in the longitudinal direction 12a, that is to say the length of the second carrier element 12, is changed.

The third carrier element 13 has a longitudinal axis 13a extending in the longitudinal direction of the third carrier element 13, a first end 13d of the third carrier element 13 and a second end 13e of the third carrier element 13. The third carrier element 13 is embodied as rotatable relative to the second connecting element 22 about the longitudinal axis 13a. The second end 13e of the third carrier element 13 can be rotatable in particular with respect to the first end 13d of the third carrier element 13 about the longitudinal axis 13a of the third carrier element. In this case, only the second end 13e of the third carrier element 13 is therefore rotatable relative to the second connecting element 22, while the first end 13d of the third carrier element 13 is not rotatable relative to the second connecting element 22. For this purpose, the first end 13d has a stator 13s, while the second end 13e has a rotor 13r. In the case shown in FIG. 1, only a part of the third carrier element 13 is therefore embodied as rotatable relative to the second connecting element 22 about the longitudinal axis 13a extending in the longitudinal direction of the third carrier element 13. The alternative case is also conceivable, whereby the entire third carrier element 13 is embodied as rotatable relative to the second connecting element 22 about the longitudinal axis 13a extending in the longitudinal direction of the third carrier element 13. In principle, it is also conceivable in another embodiment that the distance between the second connecting element 22 and the retaining device which can be connected to the third carrier element 13 is variable. For example, the third carrier element 13 can be embodied as telescopic and/or as displaceable relative to the second connecting element 22.

The first carrier element 11, the second carrier element 12 and the third carrier element 13 are embodied as rod-shaped along the respective longitudinal directions 11a, 12a and 13a. However, the first carrier element 11, the second carrier element and the third carrier element 13 can for example assume different shapes independently of one another, such that in particular the first carrier element 11, the second carrier element 12 and the third carrier element 13 can have a dogleg or an L shape or a further suitable shape.

The second carrier element 12 is connected to the first carrier element 11 via the first connecting element 21 at an angle not equal to 0 and less than 180°. In this case the angle can be adjusted via a rotation of the second carrier element 12 with respect to the first carrier element 11 via the revolute joint 23. The longitudinal axis 11a of the first carrier element 11 and the longitudinal axis 12a of the second carrier element 12 therefore form a first plane. Because the first connecting element 21 has the revolute joint 23, the first plane is identical to a first plane of rotation of the revolute joint 23. The second carrier element 12 can therefore be rotated relative to the first carrier element 11 via the revolute joint 23 about an axis of rotation 23b within the first plane of rotation of the revolute joint 23. The axis of rotation 23b is the point of intersection of the longitudinal axis 11a of the first carrier element 11 and the longitudinal axis 12a of the second carrier element 12b. The angle between the first carrier element 11 and the second carrier element 12 is therefore variable.

The third carrier element 13 is connected to the second carrier element 12 via the second connecting element 22 at an angle not equal to 0 and less than 180°. The angle between the second carrier element 12 and the third carrier element 13 is constant. The longitudinal axis 12a of the second carrier element 12 and the longitudinal axis 13a of the third carrier element 13 therefore form a second plane, the second plane being identical to the first plane. The longitudinal axis 11a of the first carrier element 11, the longitudinal axis 12a of the second carrier element 12 and the longitudinal axis 13a of the third carrier element 13 therefore lie in the first plane of rotation of the revolute joint 23. The system axis 15 is contained in the first plane of rotation of the revolute joint 23. This enables the third carrier element 13, in particular the second end 13e of the third carrier element, to be height-adjustable parallel to the system axis 15.

The first connecting element 21 and the second connecting element 22 have a device for connecting the respective carrier elements 11, 12, 13.

The revolute joint 23 enables the angles between the first carrier element 11 and the second carrier element 12 to be varied. Accordingly, the third carrier element 13, in particular the second end 13e of the third carrier element 13, is advantageously arranged so as to be movable along a circular path 30a, which is part of a circle of rotation 30, via the first carrier element 11, the revolute joint 23 and the second carrier element 12.

For example, the second end 13e can be moved along the circle of rotation 30 when the distance between the suspension device 14 and the first connecting element 21 and the distance between the first connecting element 21 and the second connecting element 22 become greater and at the same time the angle between the first carrier element 11 and the second carrier element 12 becomes smaller.

Figure 2:
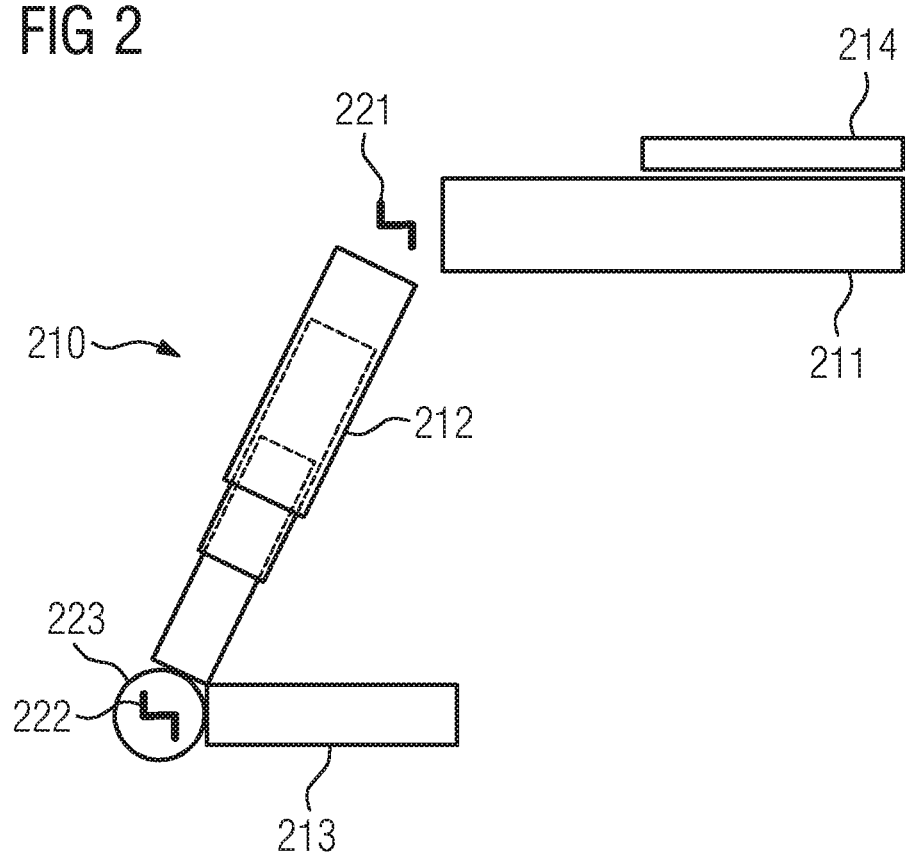
FIG. 2 shows a second embodiment variant of a carrying device.

FIG. 2 shows a second embodiment variant of a carrying device 210. For clarity of illustration reasons, only the essential differences compared to the first embodiment variant shown in FIG. 1 are labeled with reference signs in FIG. 2. The following descriptions are therefore restricted substantially to the differences compared to the example embodiment of FIG. 1.

The carrying device 210 for a retaining device for an X-ray tube assembly and an X-ray detector of an X-ray system comprises a suspension device 214, a first carrier element 211 arranged on the suspension device 214, a second carrier element 212 and a first connecting element 221. The second carrier element 212 is connected to the first carrier element 211 via the first connecting element 221. In addition, the carrying device 210 has a third carrier element 213 which can be connected to the retaining device, and a second connecting element 222, the third carrier element 213 being connected to the second carrier element 212 via the second connecting element 222.

The difference compared to FIG. 1 is that the second connecting element 222 has the revolute joint 223, whereas in FIG. 1 it is the first connecting element 21 that has the revolute joint 23. As a result it is possible to vary an angle between the second carrier element 212 and the third carrier element 213 in a second plane of rotation of the revolute joint 223. The second plane of rotation is formed by a longitudinal axis extending in the longitudinal direction of the second carrier element 212 and a longitudinal axis extending in the longitudinal direction of the third carrier element 213. A second axis of rotation of the revolute joint 223 stands perpendicularly on the second plane of rotation. The third carrier element 213 can be rotatable relative to the second carrier element 212 about the second axis of rotation of the revolute joint 223.

The carrying device 210 of FIG. 2 has substantially the same functions and characteristics as the carrying device 10 from FIG. 1.

Figure 3:
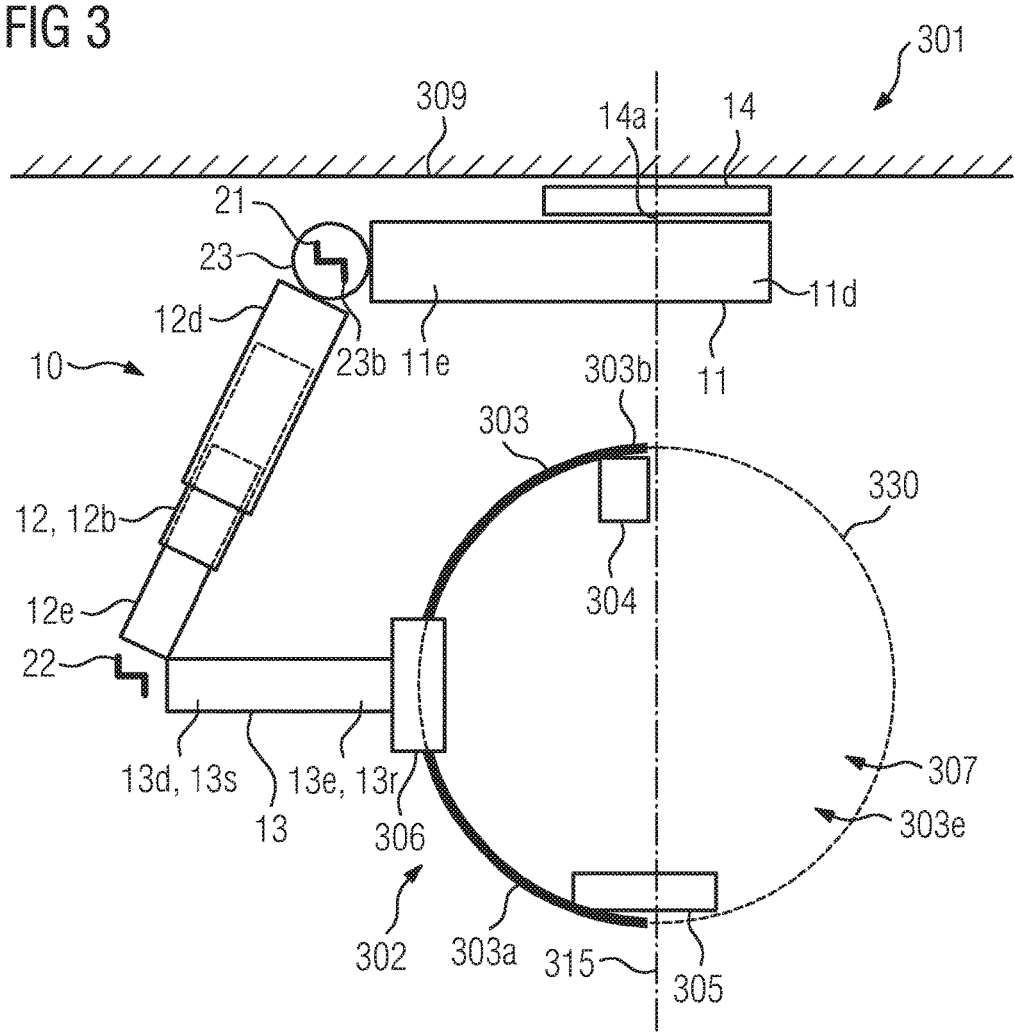
FIG. 3 shows an embodiment variant of an X-ray system.

FIG. 3 shows an embodiment variant of an X-ray system 301. The embodiment variant of the X-ray system 301 shown in FIG. 3 has the carrying device 10 according to FIG. 1, so a repetition of the description of the carrying device 10 is dispensed with.

In addition to the carrying device 10, the X-ray system 301 has a retaining device 302 connected to the third carrier element 13 of the carrying device 10. The retaining device 302 has a C-arm 303, at the ends of which an X-ray tube assembly 304 and an X-ray detector 305 are arranged, and a connecting device 306. The X-ray tube assembly 304 and the X-ray detector 305 are arranged so as to be movable exclusively via a movement of the C-arm 303 relative to the connecting device 306 along a first path 630a predefined by the shape of the C-arm 303, which first path 630a is part of a circle of rotation 330 and the arc length of which corresponds to a first angle. A first end 303a of the C-arm 303 has the X-ray detector 305 and a second end 303b of the C-arm 303 has the X-ray tube assembly 304. The circle of rotation 330 is situated in a C-arm plane 303e predefined by the shape of the C-arm 303. The circle of rotation 330 corresponds to an orbital circle of rotation of the retaining device 302 along which an orbital movement of the retaining device 302 is possible.

The X-ray system 301 has a system axis 315 which, when the carrying device 10 is suspended from a ceiling 309, stands perpendicularly on the ceiling 309 and extends through the suspension device 14, the retaining device 302 being height-adjustable along the system axis 315 via the carrying device 10. The system axis 315 of the X-ray system 301 is identical to the system axis 15 of the carrying device 10. The retaining device 302 is therefore height-adjustable along the system axis 315 via the first carrier element 11, the revolute joint 23 and the second carrier element 12.

The X-ray system 301 is arranged, in particular fixed, on the ceiling 309 via the suspension device 14 in such a way that the carrying device 10 is suspended from the ceiling 309. The suspension device 14 is additionally mounted so as to be movable on rails (not shown) of a first rail plane and on rails (not shown) of a second rail plane. The longitudinal axes extending in the longitudinal direction of the rails of the first rail plane and the second rail plane stand perpendicularly on one another. The first rail plane and the second rail plane are plane-parallel to the ceiling 209 and the system axis 315 of the X-ray system 301 stands perpendicularly thereon.

An X-ray unit 307 comprises the X-ray tube assembly 304 and the X-ray detector 305. The distance between the X-ray tube assembly 304 and the X-ray detector 305 is variable, for example when the X-ray unit has a telescope unit. A height-adjustable patient couch is not shown. Thanks to the height adjustability of the X-ray system 301 and the height-adjustable patient couch, a user is able to choose an optimal position and orientation of the X-ray system 301 and the height-adjustable patient couch for the treatment of a patient positioned on the patient couch.

The retaining device 302 is connected to the third carrier element 13 in such a way that the third carrier element 13, in particular the second end 13e of the third carrier element 13, is movable in combination with the retaining device 302 in the examination room. For example, a height adjustability of the retaining device 302 via the carrying device 10 follows from the height adjustability of the third carrier element 13 via the carrying device 10. In a further embodiment, the retaining device 302 can be rotated analogously to the second end 13e of the third carrier element 13 relative to the second connecting element 22 about the longitudinal axis 13a of the third carrier element 13.

Particularly advantageous configurations of the X-ray system 301 require both a specific configuration of the carrying device 10 and simultaneously a specific configuration of the retaining device 302. In FIG. 3, the circle of rotation 330 of the retaining device 302 corresponds to the circle of rotation 30 of the third carrier element 13. For example, this enables the retaining device 302 to be moved on the same circle of rotation 330 as the third carrier element 13. The X-ray system 301 enables this both via a specific configuration of the carrying device 10 and via a different configuration of the retaining device 302. In the latter case, the X-ray tube assembly 304 and the X-ray detector 305 can for example be moved on the circle of rotation 330 without any movement of the first carrier element 11, the revolute joint 23 and the second carrier element 12.

The following movement options are possible via the X-ray system 301 shown in FIG. 3:

a movement of the carrying device 10 in the longitudinal direction of the height-adjustable patient couch via the suspension device 14, a movement of the carrying device 10 perpendicularly to the longitudinal direction of the height-adjustable patient couch via the suspension device 14, a rotary movement of the carrying device 10 about the system axis 15 through up to +/−135°, a rotation of the retaining device 302 about the angular axis corresponding to the longitudinal axis 13a in the range from −190° up to +120°, an orbital movement of the X-ray unit 307 along the circle of rotation 330 through at least 200°, a variation of the distance between the X-ray tube assembly 304 and the X-ray detector from 900 to 1300 mm, and a rotation of the X-ray detector 305 through up to 360° about an X-ray detector axis (not shown) which stands perpendicularly on the X-ray detector surface.

Figure 4:
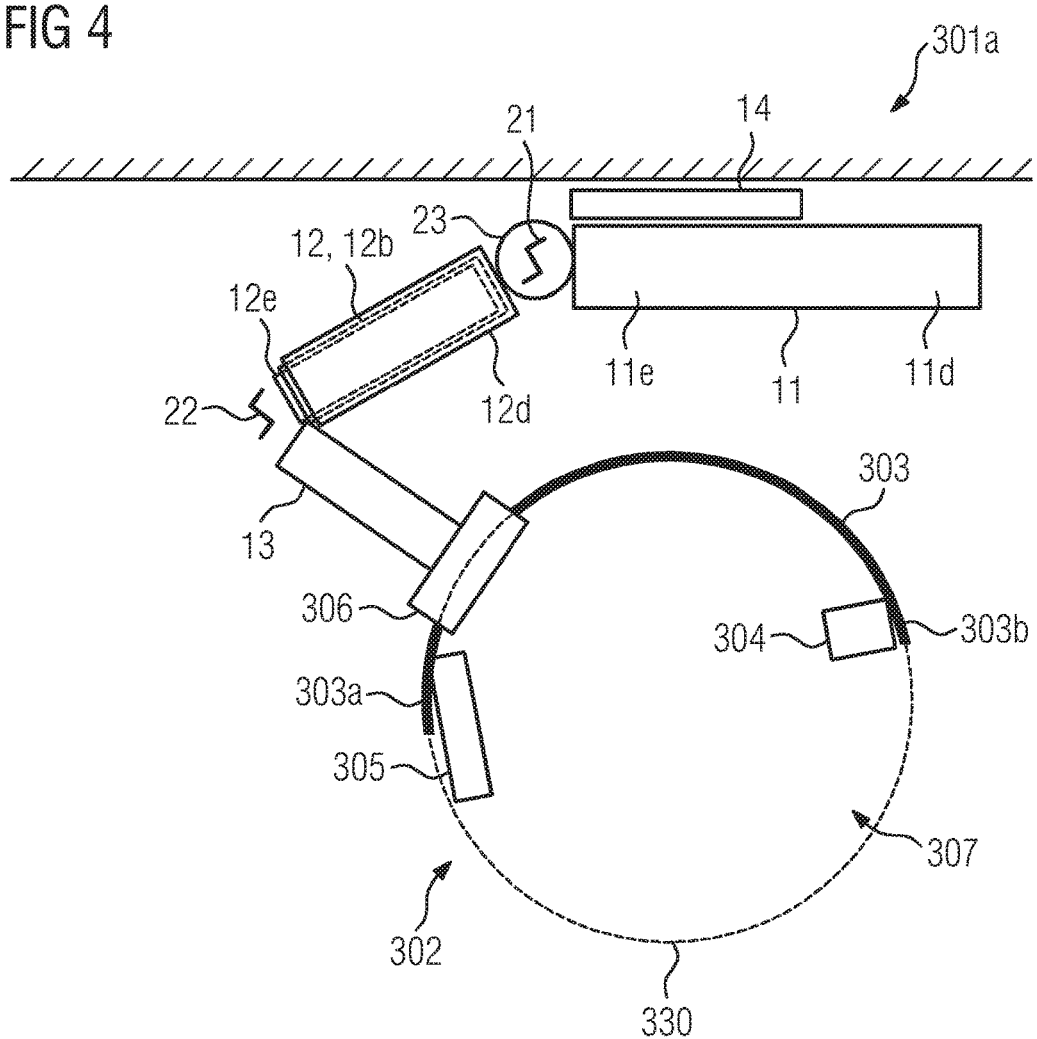
FIG. 4 shows a first extreme position of the X-ray system.
Figure 5:
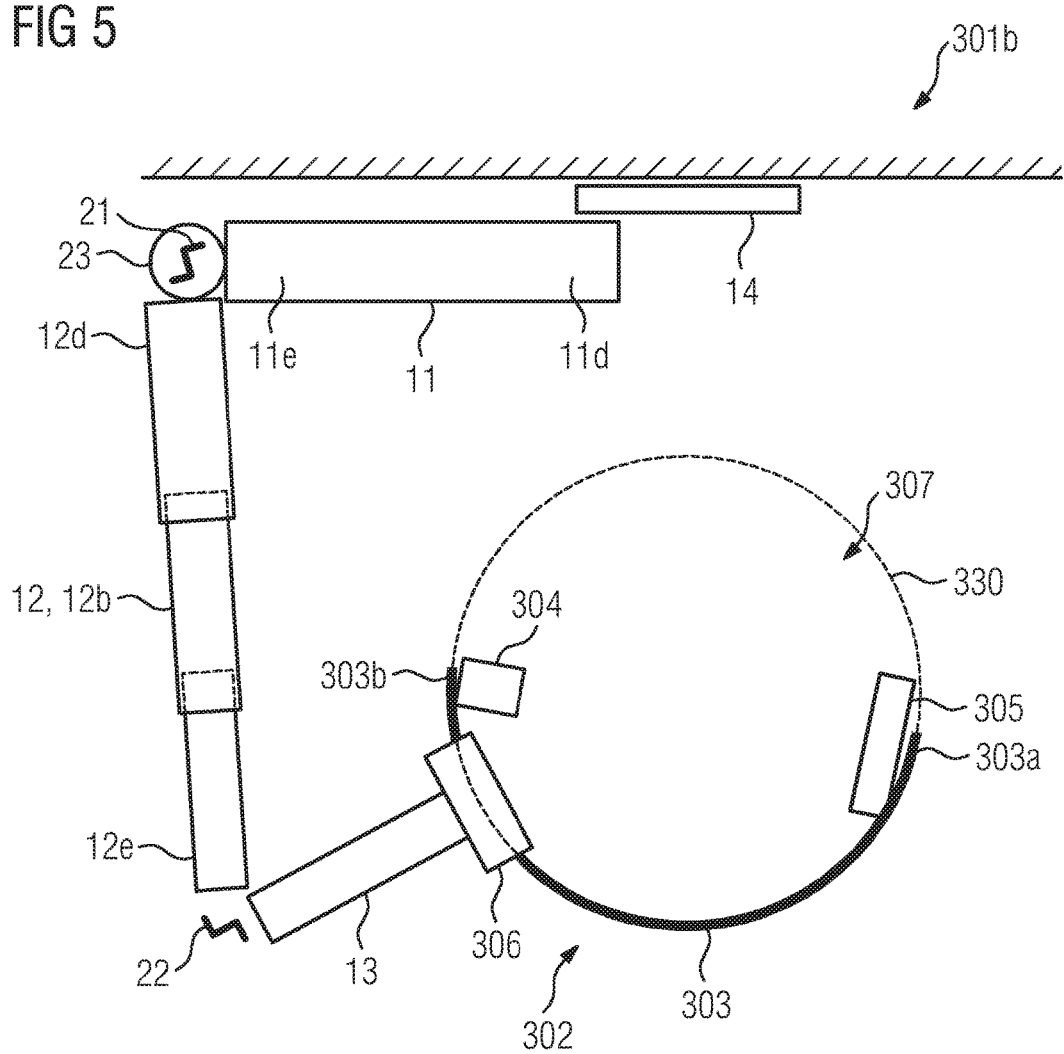
FIG. 5 shows a second extreme position of the X-ray system.

FIG. 4 shows a first extreme position 301a of the X-ray system 301, while FIG. 5 shows a second extreme position 301b of the X-ray system 301.

The X-ray system 301 is accordingly disposed in a first extreme position 301a in FIG. 4, and in a second extreme position 301b in FIG. 5. In the respective extreme positions 301a, 301b of the X-ray system 301, the X-ray unit 307, i.e. the X-ray tube assembly 304 and the X-ray detector 305, is likewise disposed in an extreme position on the circle of rotation 330.

The following configurations contribute to the situation whereby the X-ray unit 307 as shown in FIG. 4 is disposed in the first extreme position 301a:

The first carrier element 11 is configured in such a way that the distance between the suspension device 14 and the first connecting element 21, in particular the distance between the suspension device 14 and the second end 11e of the first carrier element 11, is at a minimum.

The angle of the first revolute joint 23 between the first carrier element 11 and the second carrier element 12 is greater compared to a position on the circle of rotation 330 which does not correspond to the first extreme position 301a, wherein the direction of rotation is defined such that the angle is less than 180° and positive.

The second carrier element 12 is configured in such a way that the distance between the first connecting element 21 and the second connecting element 22, in particular the distance between the first end 12d of the second carrier element 12 and the second end 12e of the second carrier element 12, is at a minimum.

The retaining device 302 is moved such that the distance from the first end 303a of the C-arm 303 to the third carrier element 13, in particular the distance from the first end 303a of the C-arm 303 to the connecting device 306, is at a minimum. The telescope unit 12b is retracted.

As an alternative to the case shown in FIG. 4, it is also possible that only some of the cited configurations contribute to the situation whereby the X-ray unit 307 as shown in FIG. 4 is disposed in the first extreme position 301a.

The following configurations contribute to the situation whereby the X-ray unit 307 as shown in FIG. 5 is disposed in the second extreme position 301b:

The first carrier element 11 is configured in such a way that the distance between the suspension device 14 and the first connecting element 21, in particular the distance between the suspension device 14 and the second end 11e of the first carrier element 11, is at a maximum.

The angle of the first revolute joint 23 between the first carrier element 11 and the second carrier element 12 is smaller compared to a position on the circle of rotation 330 which does not correspond to the second extreme position 301b, wherein the direction of rotation is defined such that the angle is less than 180° and positive.

The second carrier element 12 is configured in such a way that the distance between the first connecting element 21 and the second connecting element 22, in particular the distance between the first end 12d of the second carrier element 12 and the second end 12e of the second carrier element 12, is at a maximum.

The retaining device 302 is moved such that the distance from the first end 303a of the C-arm 303 to the third carrier element 13, in particular the distance from the first end 303a of the C-arm 303 to the connecting device 306, is at a maximum. The telescope unit 12b is extended.

As an alternative to the case shown in FIG. 5, it is also possible that only some of the cited configurations contribute to the situation whereby the X-ray unit 307 as shown in FIG. 5 is disposed in the second extreme position 301b.

FIG. 6 shows a circle of rotation of the retaining device 302. The circle of rotation 330 corresponds to the orbital circle of rotation of the orbital movement of the retaining device 302. The X-ray tube assembly 304 and the X-ray detector 305, in particular also the X-ray unit 307, are movable along the first path 630a predefined by the shape of the C-arm 303 exclusively via a movement of the C-arm 303 relative to the connecting device 306.

The X-ray tube assembly 304 and the X-ray detector 305 are arranged so as to be movable via the first carrier element 11, the revolute joint 23, the second carrier element 12 and the movement of the C-arm 303 relative to the connecting device 306 along a second path 630b which is part of the circle of rotation 330 and the arc length of which corresponds to a second angle. The second angle of the second path 630b is greater than the first angle of the first path 630a. This means in particular that the retaining device 302 per se, but also individual parts of the retaining device 302, such as, for example, the C-arm 303, the X-ray unit 307, the X-ray tube assembly 304 and/or the X-ray detector 305, is or are movable along the second path 630b. The second angle equals at least 200°.

Although the invention has been illustrated and described in greater detail on the basis of the preferred example embodiment, the invention is not limited by the disclosed examples. Variations can be derived herefrom by the person skilled in the art without departing from the scope of protection of the invention, as defined by the following claims.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An X-ray apparatus, comprising:
   a carrying device for a retaining device for an X-ray tube assembly and an X-ray detector of an X-ray system, the carrying device including:
   a suspension device;
   a first carrier element arranged on the suspension device;
   a second carrier element;
   a first connecting element, the second carrier element being connected to the first carrier element via the first connecting element;
   a third carrier element, connectable to the retaining device; and
   a second connecting element, the third carrier element being connected to the second carrier element via the second connecting element, the retaining device being connected to the third carrier element via a connecting device, the retaining device including a C-arm, wherein the X-ray tube assembly and the X-ray detector are respectively arranged at respective ends of the C-arm;
   wherein at least one of the first connecting element and the second connecting element include a revolute joint,
   a distance between the suspension device and the first connecting element being variable via the first carrier element and a distance between the first connecting element and the second connecting element being variable via the second carrier element, and
   wherein the X-ray tube assembly and the X-ray detector are arranged so as to be movable via a movement of the C-arm relative to the connecting device along a first path, defined by a shape of the C-arm and part of a circle of rotation, and
   wherein an arc length of the C-arm corresponds to a first angle and wherein the X-ray tube assembly and the X-ray detector are arranged so as to be movable via the first carrier element, the revolute joint, the second carrier element and movement of the C-arm relative to the connecting device along a second path, the second path being part of the circle of rotation and an arc length of the second path corresponding to a second angle, the second angle being relatively greater than the first angle.

2. The X-ray apparatus of claim 1, wherein the first connecting element includes the revolute joint.

3. The X-ray apparatus of claim 1, wherein the second connecting element includes the revolute joint.

4. The X-ray apparatus of claim 1, wherein the first carrier element is embodied as at least one of telescopic and displaceable relative to the suspension device.

5. The X-ray apparatus of claim 1, wherein the second carrier element is embodied as at least one of telescopic and displaceable relative to the first connecting element.

6. The X-ray apparatus of claim 1, wherein the first carrier element and the second carrier element are embodied as telescopic.

7. The X-ray apparatus of claim 1, wherein the carrying device includes a system axis which, when the carrying device is suspended from a ceiling or anchored to a floor, stands perpendicularly on the ceiling or the floor and extends through the suspension device, and wherein the first carrier element is mounted on the suspension device so as to be rotatable about the system axis.

8. The X-ray apparatus of claim 1, wherein the third carrier element is embodied as rotatable relative to the second connecting element about a longitudinal axis extending in a longitudinal direction of the third carrier element.

9. An X-ray system, comprising:
the X-ray tube assembly;
the X-ray detector
the X-ray apparatus of claim 1; and
the retaining device, connected to the third carrier element, including a C-arm, the X-ray tube assembly and the X-ray detector being respectively arranged at respective ends of the C-arm.

10. The X-ray apparatus of claim 4, wherein the second carrier element is embodied as at least one of telescopic and displaceable relative to the first connecting element.

11. The X-ray apparatus of claim 10, wherein the carrying device includes a system axis which, when the carrying device is suspended from a ceiling or anchored to a floor, stands perpendicularly on the ceiling or the floor and extends through the suspension device, and wherein the first carrier element is mounted on the suspension device so as to be rotatable about the system axis.

12. The X-ray apparatus of claim 7, wherein the third carrier element is embodied as rotatable relative to the second connecting element about a longitudinal axis extending in a longitudinal direction of the third carrier element.

13. An X-ray system comprising:
an X-ray tube assembly;
an X-ray detector;
a carrying device including
a suspension device,
a first carrier element arranged on the suspension device,
a second carrier element,
a first connecting element, the second carrier element being connected to the first carrier element via the first connecting element,
a third carrier element, and
a second connecting element, the third carrier element being connected to the second carrier element via the second connecting element,
wherein at least one of the first connecting element and the second connecting element include a revolute joint, a distance between the suspension device and the first connecting element being variable via the first carrier element and a distance between the first connecting element and the second connecting element being variable via the second carrier element; and
a retaining device, connected to the third carrier element via a connecting device and including a C-arm, the X-ray tube assembly and the X-ray detector being respectively arranged at respective ends of the C-arm,
wherein the X-ray tube assembly and the X-ray detector being arranged so as to be movable via a movement of the C-arm relative to the connecting device along a first path, defined by a shape of the C-arm and part of a circle of rotation,
wherein an arc length of the C-arm corresponds to a first angle and wherein the X-ray tube assembly and the X-ray detector are arranged so as to be movable via the first carrier element, the revolute joint, the second carrier element and movement of the C-arm relative to the connecting device along a second path, the second path being part of the circle of rotation and an arc length of the second path corresponding to a second angle, the second angle being relatively greater than the first angle.

14. The X-ray system of claim 13, wherein the carrying device includes a system axis which, when the carrying device is suspended from a ceiling or anchored to a floor, stands perpendicularly on the ceiling or the floor and extends through the suspension device, and wherein the retaining device is height-adjustable along the system axis via the carrying device.

15. The X-ray system of claim 14, wherein the retaining device is height-adjustable along the system axis via the first carrier element, the revolute joint and the second carrier element.

16. The X-ray system of claim 13, wherein a distance between the X-ray tube assembly and the X-ray detector is variable.

17. The X-ray system of claim 13, wherein the second angle equals at least 200°.

* * * * *